(12) United States Patent
Kojima et al.

(10) Patent No.: US 7,732,149 B2
(45) Date of Patent: Jun. 8, 2010

(54) METHODS OF SCREENING AGONISTIC ANTIBODIES

(75) Inventors: Tetsuo Kojima, Shizuoka (JP); Chiaki Senoo, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 922 days.

(21) Appl. No.: 10/511,993

(22) PCT Filed: Apr. 25, 2003

(86) PCT No.: PCT/JP03/05372

§ 371 (c)(1), (2), (4) Date: Mar. 28, 2005

(87) PCT Pub. No.: WO03/091424

PCT Pub. Date: Nov. 6, 2003

(65) Prior Publication Data

US 2005/0164307 A1    Jul. 28, 2005

(30) Foreign Application Priority Data

Apr. 26, 2002  (JP) .............................. 2002-127260

(51) Int. Cl.
*G01N 33/53* (2006.01)
(52) U.S. Cl. ...................... 435/7.2; 435/375; 530/387.1
(58) Field of Classification Search .................. None
See application file for complete search history.

(56) References Cited

FOREIGN PATENT DOCUMENTS

| GB | 2344886 | 6/2000 |
|---|---|---|
| WO | WO 98/50431 | 11/1998 |
| WO | WO 99/10494 | 3/1999 |
| WO | WO 99/38008 | 7/1999 |
| WO | WO 03/091424 | 6/2003 |

OTHER PUBLICATIONS

Xie M.H. et al., "Direct demonstration of MuSK involvement in acetylcholine receptor clustering through identification of agonist ScFv.", Nature Biotechnology, vol. 15(8), pp. 768-771 (1997).
Rowlinson S.W. et al., "Activation of Chimeric and Full-length Growth Hormone Receptors by Growth Hormone Receptor Monoclonal Antibodies", J. Biol. Chem., vol. 273(9), pp. 5307-5314 (1998).

Takahashi T. et al., "Swapping between Fas and Granuloctye Colony-stimulating Factor Receptor", J. Biol. Chem., vol. 271(29), pp. 17555-17560 (1996).
Shneider H. et al., "Homodimerization of erythropoietin receptor by a bivalent monoclonal antibody triggers cell proliferation and differentiation of eithroid precursors", Proc. Natl. Acad. Sci. USA, vol. 89(2), pp. 473-482 (1977).
Prat M. et al., "Agonistic monoclonal antibodies against the Met receptor dissect the biological responses to HGF", Journal of Cell Science, vol. 111(2), pp. 237-247 (1998).
Kitamura T. et al., "Efficient screening of retroviral cDNA expression libraries", Proc. Natl. Acad. Sci. USA, vol. 92(20), pp. 9146-9150 (1995).
Onishi M. et al., "Applications of retrovirus-mediated expression cloning", Experimental Hematology, vol. 24(2), pp. 324-329 (1996).
Ridgway J.B. et al., "Knobs-into-holes" engineering of antibody $C_H3$ domains for heavy chain herterodimerization, Protein Engineering, vol. 9(7), pp. 617-621 (1996).
Carter, "Bispecific human IgG by design," *J. Immunol. Methods*, 248:7-15 (2001).
Deng et al., "An Agonist Murine Monoclonal Antibody to the Human c-Mpl Receptor Stimulates Megakaryocytopoiesis," *Blood*, 92:1981-1988 (1998).
Francois et al., "Construction of a Bispecific Antibody Reacting with the α- and β-Chains of the Human IL-2 Receptor," *J. Immunol.*, 150:4610-4619 (1993).
Kim et al., "Mammalian type I interferon receptors consists of two subunits: IFNaR1 and IFNaR2," *Gene*, 196:279-286 (1997).
Lu et al., "Fab-scFv fusion protein: an efficient approach to production of bispecific antibody fragments," *J. Immunol. Methods*, 267:213-226 (2002).
Rajpal et al., "Intracellular Stability of Anti-caspase-3 Intrabodies Determines Efficacy in Retargeting the Antigen," *J. Biol. Chem.*, 276:33139-33146 (2001).
Segal et al., "Introduction: bispecific antibodies," *J. Immunol. Methods*, 248:1-6 (2001).
Tse et al., "Intracellular Antibody Capture Technology: Application to Selection of Intracellular Antibodies Recognising the BCR-ABL Oncogenic Protein," *J. Mol. Biol.*, 317:85-94 (2002).

*Primary Examiner*—Michael Pak
(74) *Attorney, Agent, or Firm*—Fish & Richardson P.C.

(57) ABSTRACT

Cell strains with ligand-dependent (factor-dependent) proliferation are super-infected with antibody libraries against each of the various receptor chains. Antibody genes are recovered from strains that autonomously grow by the autocrine stimulation by agonistic antibodies formed by appropriate combinations, enabling effective screening of agonistic antibodies. In this method, effective screening can be carried out using antibodies as libraries. Furthermore, the manipulations are simple, and there is no need for complicated operations.

15 Claims, 1 Drawing Sheet

SEQUENCE LISTING

<160> NUMBER OF SEQ ID NOS: 14

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 1
ggaattcgcc gccaccatgg agtttgggct gagctgggtt ttcct            45

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 2
gcatgcatgg cccccgaggc cactcacctt tgatctccag cttggtccct ccgccgaa    58

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 3
ggcggcggcg gctccggtgg tggtggatcc caggtgcagc tggtgcagtc tgg         53

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 4
gcatgcatgg cccccgaggc cactcacctg aagagacggt gaccattgtc cctt         54

```
<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 5
agtcagtcgg cccagccggc catggcggac tacaaagaca tccagatgac ccagtctcct    60

<210> SEQ ID NO 6
<211> LENGTH: 76
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
ggagccgccg ccgccagaac caccaccacc agaaccacca ccacctttga tctccagctt    60
ggtccctccg ccgaaa                                                    76

<210> SEQ ID NO 7
<211> LENGTH: 57
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
tcgaattcgg cctcgggggc cagctttctg gggcaggcca ggcctgacct tggcttt       57

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
cacggtgggc atgtgtgagt tttgtcacaa gatttgggct caactttctt gtccaccttg    60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
caaaactcac acatgcccac cgtgcccagc acctgaactc ctgggggac cgtcagtctt     60

<210> SEQ ID NO 10
<211> LENGTH: 53
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
acacctgtgg ttctcggggc tgcccttttgg ctttggagat ggttttctcg atg          53
```

```
<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
ggcagccccg agaaccacag gtgtacaccc                                        30

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
tagcggccgc tcatttaccc ggagacaggg agaggctctt                             40

<210> SEQ ID NO 13
<211> LENGTH: 42
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
cggaattcgg ccggctgggc cagcatcagg agcaggagca gc                          42

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
gcggatccgc cgccaccatg gttcttgcca gctctac                                37
```

METHODS OF SCREENING AGONISTIC ANTIBODIES

TECHNICAL FIELD

The present invention relates to novel methods of screening for agonistic antibodies.

BACKGROUND ART

Antibodies in the blood are highly stable, and since they have no antigenicity, they are drawing much attention as pharmaceuticals. Of these, it has been a while since bispecific antibodies, which can simultaneously recognize two types of antigens, have been proposed, but only those that merely bind two types of antigens exist at present. However, since antibodies bind to specific epitopes within antigens, it may be possible to place two antigens at desirable distances and angles by selecting appropriate antibody combinations.

In many cytokine receptors, it is thought that the angle and length of chains that form homo/hetero-dimers change when a ligand binds, thus enabling the receptors to transmit signals into cells. Thus, appropriate anti-receptor antibodies can mimic receptor dimerization initiated by ligand-binding, and become potential agonistic antibodies. Monoclonal antibodies that display agonistic activity against MPL, a homodimer, have already been reported (Blood 1998 Sep. 15; 92(6): 1981-8, US98/17364). However, to obtain such agonistic antibodies, selection must be made from a huge range of antibodies, requiring effective selection methods.

In conventional assays, it is necessary to select antibodies that bind to antigens, i.e., receptor chains, and add these antibodies to an appropriate cell assay system that responds to the ligands. This becomes particularly troublesome where the receptors form heterodimers. Antibodies against each of the two chains (A, B) that form the receptor must be selected, and every combination of A and B must be tested one by one. In addition, to generate bivalent antibodies, it is necessary to fuse antibody-producing hybridomas, or to construct expression vectors for all of the antibodies, and introduce all combinations thereof into cells. Examination of 100 types of antibodies against each of the A and B chains necessitates the testing of 10,000 types of combinations, and requires a total of 400 types of expression vectors for L and H chains to be constructed and introduced into cells 10,000 times. There are also methods that use libraries that provide antibodies displayed on phages as bispecific diabodies. However, since the direct addition of *E. coli* culture supernatant to cell culture systems has a bad effect on cells, purification becomes necessary and monospecific diabody contamination (theoretically 50%) becomes inevitable.

DISCLOSURE OF THE INVENTION

The present invention was achieved in view of the above. An objective of the present invention is to provide efficient novel methods of screening for agonistic antibodies, especially multi-specific agonistic antibodies. More specifically, it aims to provide methods of screening for agonistic antibodies that utilize autocrine cell growth.

With the above objective, the present inventors conducted extensive experiments. As a result, they discovered effective methods of screening for agonistic antibodies, such as the methods below. In these methods, cell strains that proliferate in a ligand-dependent manner are infected with anti-receptor antibody libraries. Antibody genes are recovered from strains that replicate autonomously upon autocrine stimulation due to the binding of agonistic antibodies, and agonistic antibodies are prepared based on the recovered genes. When the antibodies are multi-specific agonistic antibodies, cell strains with ligand-dependent growth are super-infected with antibody libraries against each of the various receptor chains. Antibody genes are recovered from strains that replicate autonomously upon autocrine stimulation due to the binding of the multi-specific agonistic antibodies in appropriate combinations, and multi-specific agonistic antibodies are generated based on the recovered genes. More specifically, this can be carried out, for example, as follows:

Mice are first immunized with either A-chain or B-chain receptors, and mRNAs are extracted from the splenocytes of these animals. L-chain and H-chain variable regions are recovered by RT-PCR using primers that correspond to mouse CDRs. Single chain variable regions (scFvs) are synthesized by assembly PCR to construct a phage library. Antigen-binding antibody clones are concentrated by panning, the synthesized single chain variable regions obtained from concentrated clones are inserted between a signal sequence for animal cells and CH1-hinge-CH2-CH3 and, to construct a library that is integrated into plasmids to be used for producing retroviruses. By expressing chimeric chains comprised of a target receptor chain and the G-CSFR intracellular domain, Ba/F3 cells, whose proliferation depends on the binding of the ligand to target chimera receptor, are prepared. These cells are infected with anti-A-chain antibody library viruses. These cells are further infected with anti-B-chain antibody library viruses, and cultured following the washing and removal of ligands (factors). Cells that now reproduce ligand (factor)-dependently are recovered and cloned, and agonistic activity is confirmed by using the culture supernatants and physiological assay systems. The antibody CDR genes incorporated in the chromosomes of the clones are recovered using PCR, and applied to the production of multi-specific agonistic antibodies. In this method, effective screening can be carried out using antibodies as libraries. Furthermore, the manipulations are simple, and there is no need for complicated operations.

As described above, the present inventors developed novel methods that can effectively screen for agonistic antibodies, thus completing the present invention.

In other words, the present invention relates to novel methods that can effectively screen for multi-specific agonistic antibodies. More specifically, the present invention provides:

[1] a method of screening for agonistic antibodies that comprises the following steps (a) to (c):

(a) providing a cell that expresses a multimer-forming receptor and a test antibody, where the cell grow depending on the corresponding ligand of the receptor;

(b) determining the test antibody to comprise agonistic activity when autocrine cell growth is autonomous; and (c) selecting those antibodies that comprise agonistic activity;

[2] the method of [1] that further comprises the step of introducing a gene that encodes the heavy chain of the test antibody into the cell of step (a) having been introduced with a gene that encodes the light chain of the test antibody and a gene that encodes the receptor;

[3] the method of [1] or [2] where the receptor is a chimeric receptor with a protein that comprises a function of transducing a cell growth signal;

[4] the method of any one of [1] to [3] where the receptor is a dimer-forming receptor;

[5] the method of [4] where the dimer-forming receptor is a homo-dimer;

[6] the method of [4] where the dimer-forming receptor is a hetero-dimer;

[7] the method of any one of [1] to [6] where the protein that comprises the function of transducing a cell growth signal is a G-CSF receptor;

[8] the method of any one of [1] to [7] that comprises the introduction of an antibody library to the cell;

[9] the method of [8] where the antibody library is a retroviral antibody library;

[10] the method of any one of [1] to [9] where the test antibody is a multi-specific antibody;

[11] the method of [10] that comprises linking the test antibody's heavy and light chain variable regions with a linker;

[12] the method of [11] that comprises producing the antibody with variable regions linked by a linker, using a method that comprises the steps (a) to (c):

(a) producing a single chain Fv against the first receptor chain;

(b) producing a single chain antibody against the first receptor chain by linking the single chain Fv with a CH1-hinge-CH2-CH3; and (c) producing a multi-specific antibody that comprises the single chain antibody produced in step (b);

[13] the method of [11] that comprises producing the antibody with its variable regions linked by a linker, using a method that comprises the steps (a) to (c):

(a) producing a single chain Fab against the first receptor chain;

(b) producing a single chain antibody against the first receptor chain by linking the single chain Fab with an Fc; and (c) producing a multi-specific antibody that comprises the single chain antibody produced in step (b);

[14] a method of screening for an agonist multi-specific antibody that comprises the steps (a) to (c):

(a) contacting between a multi-specific antibody and a receptor comprising a first receptor chain and a second receptor chain, where the multi-specific antibody comprises a variable region that can bind with the first receptor chain and a variable region that can bind with the second receptor chain;

(b) determining whether the test multi-specific antibody comprises agonistic activity; and (c) selecting antibodies that comprise agonistic activity;

[15] the method of [14] that comprises expressing the receptor and the test multi-specific antibody in the same cell;

[16] the method of [15] where the cell is a cell that grows depending on the corresponding ligand of the receptor;

[17] the method of [15] or [16] where the receptor comprises the function of transducing a cell growth signal;

[18] the method of [17] where the receptor is a chimeric receptor with a protein that comprises the function of transducing a cell growth signal;

[19] the method of [18] where the protein that comprises the function of transducing a cell growth signal is a G-CSF receptor;

[20] the method of any one of [15] to [19] where the test multi-specific antibody is determined to comprise agonistic activity when autocrine cell growth is autonomous;

[21] the method of any one of [15] to [20] that further comprises the step of introducing an antibody library against the first receptor chain and the second receptor chain into the cell, respectively;

[22] the method of [21] where the antibody library is a retroviral antibody library;

[23] the method of any one of [14] to [22] that comprises linking the light chain variable regions and heavy chain variable regions of the multi-specific antibody with a linker;

[24] the method of [23] that comprises producing a multi-specific antibody with variable regions linked by a linker, using a method that comprises steps (a) to (c):

(a) producing a single chain Fv against the first receptor chain;

(b) producing a single chain antibody against the first receptor chain by linking the single chain Fv with a CH1-hinge-CH2-CH3; and (c) producing a multi-specific antibody that comprises the single chain antibody produced in step (b);

[25] the method of [23] that comprises producing the multi-specific antibody with variable regions linked by a linker, using a method that comprises steps (a) to (c):

(a) producing a single chain Fab against the first receptor chain;

(b) producing a single chain antibody against the first receptor chain by linking the single chain Fab with an Fc; and (c) producing a multi-specific antibody that comprises the single chain antibody produced in step (b);

[26] the method of any one of [14] to [25] that comprises the introduction of "Knobs-into-holes" by amino acid substitution at the CH3 region of the multi-specific antibody;

[27] the method of any one of [14] to [26] where the multimer of the receptor is a heterodimer;

[28] the method of any one of [14] to [27] where the multi-specific antibody is a bispecific antibody;

[29] a method for producing an agonistic antibody comprising steps (a) to (c):

(a) screening for an agonistic antibody by a method of any one of [1] to [28];

(b) introducing a gene that encodes the agonistic antibody selected by the screening of step (a) into a host cell;

(c) recovering the agonistic antibody from the host cell of step (b) or its cell culture supernatant;

[30] a cell that expresses an antibody, and a receptor that multimerizes by binding with the antibody, where the cell grow depending on the corresponding ligand of the receptor;

[31] the cell of [30] where the receptor is a chimeric receptor with a protein that comprises the function of transducing a cell growth signal;

[32] the cell of [30] or [31] where the antibody is a multi-specific antibody;

[33] the cell of any one of [30] to [32] where the receptor that is multimerized by binding with the antibody comprises the function of transducing a cell growth signal;

[34] a multi-specific agonistic antibody that comprises the linking of the light chain variable region and heavy chain variable region by linkers, and the introduction of "Knobs-into-holes" by amino acid substitution at the CH3 region of the antibody.

In the present invention, set terms have been defined to simplify understanding of the terms used within the present specification. It should be understood that these definitions should not be used to limit the present invention.

The present invention provides effective novel methods of screening for agonistic antibodies. In these methods, test antibodies comprising variable regions that can bind receptors are contacted with those receptors (step (a)).

In the present invention, when the antibodies are multi-specific antibodies, multi-specific test antibodies comprising variable regions that can bind the first and second receptor chains are contacted with those receptors (step (a)).

"Agonistic antibody" refers to an antibody that comprises an agonistic activity against a given receptor. In general, when an agonist ligand (factor) binds to a receptor, the tertiary structure of the receptor protein changes, and the receptor is activated (when the receptor is a membrane protein, a cell growth signal or such is usually transducted). If the receptor is a dimer-forming type, an agonistic antibody can dimerize the receptor at an appropriate distance and angle, thus acting similarly to a ligand. An appropriate anti-receptor antibody can mimic dimerization of receptors performed by ligands, and thus can become an agonistic antibody.

"Multi-specific antibodies" refer to antibodies that can bind specifically with a number of types of antigens. That is, multi-specific antibodies are antibodies that comprise specificities to at least two different types of antigens. Usually, such molecules bind with two antigens (i.e., a bispecific antibody). However, in the present specification, "multi-specific antibody" also comprises antibodies that comprise specificities against more antigens (for example, three types). A multi-specific antibody can be a full-length antibody or a fragment thereof (for example, F(ab')$_2$ bispecific antibody). Multi-specific antibodies are useful in clinical fields such as immuno-diagnostics, therapy, and diagnoses using immunological assays. Suitable examples of the multi-specific antibodies of the present invention include bispecific antibodies that can specifically bind to two types of antigens. Usually, when the antigens are hetero-receptors, bispecific antibodies will recognize each of the two polypeptide chains that make up the hetero-receptor.

In the present invention, "multi-specific agonistic antibodies" refer to antibodies that comprise a quality (characteristic) of both the above-mentioned agonistic antibodies and multi-specific antibodies.

In a preferable embodiment of the present invention, the test antibodies for use in the screening methods of the present invention are first prepared. However, the process for preparing the test antibodies is not essential. The test antibodies can be known compounds, or antibody molecules (or antibody-like molecules) that exist in nature, or fragments thereof, and such.

In the present invention, there are no limitations as to what kinds of antibodies can be used as test antibodies, but multi-specific antibodies are preferable, and bispecific antibodies are even more preferable.

Equally, there are no particular limitations as to what kinds of receptors can be used as the receptors to which the agonistic antibodies of the present invention bind and transmit signals. Preferable examples of the receptors include cell membrane receptors, more preferably receptors that form multimers, and even more preferably receptors that form dimers (e.g., heteroreceptors).

The above-mentioned test antibodies of the present invention can usually be prepared by immunizing animals with antigens. The antigens used to immunize the animals include complete antigens that have immunogenicity, and incomplete antigens (including hapten) having no antigenicity. In the present invention, receptors for which agonistic antibodies to be screened are thought to act as ligands are used as antigens (immunogens) mentioned above. There are no specific limitations as to the above receptors, but usually they are multi-mers, and preferably dimers. Dimers include homodimers, which are made of identical receptor chains, and heterodimers, which are made of different receptor chains. Heterodimers are more preferable. Examples of the immunized animals that can be used include mice, hamsters, rhesus monkeys, and such. Immunization of these animals with the antigens can be carried out by methods known to those skilled in the art. In the present invention, the antibody L-chain and H-chain variable regions are preferably recovered from the immunized animals or cells of those animals. This process can be carried out using techniques generally known to those skilled in the art. The animals immunized by the antigens express antibodies against those antigens, particularly in splenocytes. Thus, for example, mRNA can be prepared from the splenocytes of immunized animals, and using primers that correspond to the CDR of those animals, the L-chain and H-chain variable regions can be recovered by RT-PCR. Here, "CDR" refers to three regions (CDR1, CDR2 and CDR3) that directly and complementarily bind the antigen, and are present in the hyper-variable region of antibody variable regions. Examples of primers that can be used as primers that correspond to the CDR include primers that correspond to a framework with less variation than the CDR, or primers that correspond to the signal sequences, and CH1 and CL. In addition, lymphocytes can also be immunized in vitro. After this, DNAs that encode the antibodies contained in the spleens of immunized animals, or in lymphocytes, can be isolated by conventional methods, for example, methods using nucleotide probes and such that can bind specifically to the genes encoding antibody heavy and light chains.

The receptors that act as immunogens can be the entire proteins that make up those receptors, or peptide fragments of those proteins. In a preferable embodiment of the present invention, if the receptor is a heteroreceptor, two or more different types of peptide chain fragments are used as immunogens for the peptide chain fragment making up one part of the heteroreceptor. In the present invention, the different peptide chain fragments are called the "first receptor chain" and the "second receptor chain" respectively. Where a receptor of the present invention forms a dimer, the above-mentioned "first receptor chain" and "second receptor chain" are preferably peptide chains (or fragment peptide thereof) that respectively make up each subunit of that dimer. For example, when a heterodimer is made up of two types of peptide chains, the A-chain and the B-chain, it is preferable that the A-chain (or a peptide fragment thereof) be the "first receptor chain", and the B-chain (or a peptide fragment thereof) be the "second receptor chain". By immunizing animals using these first and second receptor chains as immunogens, test antibodies can be prepared that comprise variable regions which can bind those first and second receptor chains.

Depending on the situation, the immunogens used to immunize the animals can also be soluble antigens that bind with other molecules, or fragments thereof. When using receptor-like transmembrane molecules as the antigens, it is preferable to use their fragments (for example, the extracellular region of a receptor). The immunogens can also be cells that express transmembrane molecules on the cell surface. Such cells can be naturally derived (tumor cell lines, etc.) or may be those constructed to express a transmembrane molecule using recombinant technologies.

In a preferable embodiment of the above screening methods of the present invention, cells whose growth depends on ligands (factors) of the receptors for which the agonistic antibodies act as agonists, are first infected with a viral antibody library against each of the receptors. Cells infected with that library produce anti-receptor antibodies. In the present invention, the antibodies produced by the above-mentioned cells are supplied as "test antibodies" for the screening methods of the present invention. When the antibodies are multi-specific antibodies, the cells whose growth depends on ligands (factors) of the receptors for which the agonistic antibodies act as agonists, are super-infected with viral antibody libraries against each of the different types of receptor chains. Cells infected with these libraries produce a variety of anti-receptor antibodies that arise from appropriate peptide chain combinations.

The above-mentioned cells of the present invention are usually eukaryote-derived cells, preferably animal cells, and more preferably human-derived cells. In a preferable embodiment of the present invention, cells expressing test antibodies also express the above receptors (the receptors for which agonistic antibodies act as agonists). Thus, a preferable embodiment of the present invention comprises expressing a receptor and a test antibody in the same cell. If a test antibody secreted from a cell binds with that receptor and comprises agonistic activity against a receptor, the receptor would transduce a cell growth signal and consequently, the cell would undergo autonomous autocrine replication. "Autonomous autocrine replication" refers to the phenomenon whereby cells replicate independently using a substance produced by the cell itself as a growth signal. Multi-specific agonistic antibodies can be screened using the presence or absence of autonomous autocrine replication as an index. In a preferable embodiment of the present invention, when cells expressing a test antibody and receptor undergo autonomous autocrine replication, the test antibody can be determined to comprise agonistic activity.

Agonistic activity of the test antibodies of the present invention can be determined using the indexes below:

(1) Whether or not a ligand (factor)-dependently growing cell will grow in the same way when a test antibody is added during cell culture as when a ligand (factor) is added. If the cell grows, the test antibody is determined to comprise agonistic activity.

(2) Whether or not a cell line with intrinsic ligand (factor)-dependent activities (not limited to growth) shows the same reaction when a test antibody is added during cell culture as when a ligand (factor) is added. If the cell line shows the same reaction as for a ligand (factor), the test antibody is determined to comprise agonistic activity.

In the present invention, cells transducing the above-mentioned cell growth signals usually express the receptors for which the antibodies selected by the screening methods of the present invention act as agonists on the cell surface. These cells transduce cell growth signals by binding with the ligands of those receptors (for example, agonistic antibodies). Thus, in the present invention, cells that are used are preferably cells that can proliferate receptor ligand (factor)-dependently (cells with ligand (factor)-dependent proliferation). Preferably, on binding with a ligand, the receptors of the present invention usually transduce cell growth signals. However, when the receptors of the present invention are of a type that do not transduce cell growth signals, they can be used in the present invention as so-called "chimeric receptors", by fusing with receptors of a type that do transduce cell growth signals. More specifically, a chimeric receptor that comprises an extracellular region of a ligand-binding receptor, and an intracellular region of a type of receptor that transduces cell growth signals can be used. These chimeric receptors transduce cell growth signals on binding with a ligand. Receptors suitable for constructing chimeric receptors by fusion with ligand-binding receptors are not especially limited as long as they are of a type that transduces cell growth signals. Receptors that can be used include cytokine receptors and receptors known to those skilled in the art. G-CSF receptor, mpl, neu, GM-CSF receptor, EPO receptor, c-Kit, FLT-3 and such are specific examples of such receptors. A suitable example of the above cells that grow ligand (factor)-dependently is a BaF3 ligand (factor)-dependent cell that expresses a chimeric receptor whose extracellular portion is a ligand receptor chain, and whose intracellular portion is a G-CSF receptor chain. Other examples of cells that can be used in the present invention include NFS60, FDCP-1, FDCP-9 CTLL-2, DA-1, KT-3, and such.

As described above, the present invention comprises antibodies, and cells that express receptors which multimerize on binding with those antibodies. The present invention also comprises cells whose growth is dependent on ligands (factors) against the receptor.

In the present invention, "antibodies" comprise so-called "immunoglobulins", as well as natural antibodies, antibody-like molecules, and antibody fragments. Natural antibodies and immunoglobulins are generally heterotetramers of about 150,000 Daltons consisting of two identical light chains (L chains) and two identical heavy chains (H chains). Each of the light chains is connected to a heavy chain through a single covalent disulfide bond. However, the number of disulfide bonds between the heavy chains varies depending on the isotype of the immunoglobulin. Both of the heavy and light chains further have intramolecular disulfide bridges at constant distances. Each of the heavy chains has a variable region ($V_H$) at one end and many constant regions connected thereto. Each of the light chains has a variable region ($V_L$) at one end and a constant region at the other end. The constant region and the variable region of the light chains are placed side-by-side to the first constant region and the variable region of the heavy chain, respectively. Specific amino acid residues are considered to form the interface of the variable region of the light and heavy chains (Chothia C. et al., J. Mol. Biol. 186: 651-663, 1985; Novotny J., Haber E., Proc. Natl. Acad. Sci. USA 82: 4592-4596, 1985). In the present invention, a preferable example used as a test antibody is an immunoglobulin G (IgG).

The above-mentioned phrase "antibody fragment" refers to a part of a full-length antibody and generally indicates an antigen-binding region or a variable region. For example, antibody fragments include Fab, Fab', $F(ab')_2$ and Fv fragments. Papain digestion of an antibody produces two identical antigen-binding fragments called Fab fragments each having an antigen-binding region, and a remaining fragment called "Fc" due to ready crystallization. On the other hand, pepsin digestion results in a $F(ab')_2$ fragment (which has two antigen-binding sites and can cross bind antigens) and another remaining fragment (called pFc'). Other fragments include diabody (diabodies), linear antibodies, single-chain antibodies, and multispecific antibodies formed from antibody fragments. In this specification, "antibody fragment" of an antibody indicates Fv, F(ab) and $F(ab')_2$ fragments, and such.

Herein, an "Fv" fragment is the smallest antibody fragment and contains a complete antigen recognition site and a binding site. This region is a dimer ($V_H$-$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. Six CDRs confer the antigen-binding site of an antibody. However, a variable region (or a half of Fv which contains only three CDRs specific to an antigen) alone has also the ability to recognize and bind an antigen although its affinity is lower than the affinity of the entire binding site.

Moreover, a Fab fragment (also referred to as F(ab)) further includes the constant region of the light chain and a constant region ($C_H$1) of the heavy chain. An Fab' fragment differs from the Fab fragment in that it additionally has several residues derived from the carboxyl end of the heavy chain $C_H$1 region which contains one or more cysteines from the hinge domain of the antibody. Fab'-SH indicates an Fab' wherein one or more cysteine residues of the constant region has a free thiol-group. The F(ab') fragment is produced by the cleavage of disulfide bonds between the cystines in the hinge region of the F(ab')$_2$ pepsin digest. Other chemically bound antibody fragments are also known to those skilled in art.

In the present invention, diabodies (Db) mean bivalent antibody fragments constructed by gene fusion (Holliger P. et al., Proc. Natl. Acad. Sci. USA 90: 6444-6448 (1993); EP 404,097; WO93/11161). Diabodies are dimers comprising two polypeptide chains, where each polypeptide chain comprises a light chain variable domain ($V_L$) and a heavy chain variable domain ($V_H$) connected with a linker short enough to prevent interaction of these two domains, for example a linker of about five amino acids. The $V_L$ and $V_H$ domains encoded on the same polypeptide chain will form a dimer because the linker between the $V_L$ and $V_H$ is too short to form a single chain variable region fragment. Thus, the result is a diabody that comprises two antigen-binding sites. If the $V_L$ and $V_H$ domains directed against two different antigens (a and b) are expressed simultaneously as combinations of $V_L$a-$V_H$b and $V_L$b-$V_H$a connected with a linker of about five residues, they can be secreted as a bispecific diabody.

A single-chain antibody (hereafter also described to as sc Fv) or sFv antibody fragment contains the $V_H$ and $V_L$ regions of an antibody, and these regions exist on a single polypeptide chain. Generally, an Fv polypeptide further contains a polypeptide linker between the $V_H$ and $V_L$ regions, and therefore an scFv can form a structure necessary for antigen binding. See, Pluckthun "The Pharmacology of Monoclonal Antibodies" Vol. 113 (Rosenburg and Moore eds. (Springer Verlag, New York) pp. 269-315, 1994) for a review on scFv. In the present invention, linkers are not especially limited as long as they do not inhibit expression of antibody variable regions linked at their ends.

In addition, a technology using gene engineering to create "humanized antibodies" is known. In this technology, all but the CDR of monoclonal antibodies from non-human mammals (such as mice, rats, and hamsters) is replaced with frame structure sequences of variable domains from human immunoglobulins (see for example, Jones et al., Nature 321: 522-525 (1986); Riechmann et al., Nature 332: 323-329 (1988); Presta, Curr. Op. Struct. Biol. 2: 593-596 (1992)). Humanized antibodies may comprise amino acids that are comprised in neither the CDR introduced into the recipient antibody nor the frame structure sequences. Normally, such introduction of amino acid residues is performed to optimize antibodies for more precise antigen recognition and binding. The variable domains in the test antibodies of the present invention also comprise altered variable domains, such as humanized domains.

In the present invention, suitable examples of the test antibodies that are expressed in cells by antibody libraries include IgG, antibody molecules where scFV is attached at the N-terminal of CH1-hinge-CH2-CH3, scIgG (antibody molecules where scFab is attached at the N-terminal of hinge-CH2-CH3), scDb, and such. In the present invention, usually antibody libraries against each of the different antigens are super infected into cells; however, when using scDb, a single library can be used as the antibody library.

In a preferable embodiment of the present invention, antibody libraries are introduced into cells. When the antibodies are multi-specific antibodies, antibody libraries against each of the first receptor chain and the second receptor chain are introduced into cells. Retrovirus antibody libraries, for example, can be suitably used as these antibody libraries. Retroviruses comprise the following features: retroviral infection efficiency can be controlled to about 10%, so most of the infected cells can be expected to incorporate one copy of the virus. In addition, introduced genes can be incorporated into host chromosomes, so stable expression of these genes over a long period can also be expected. Other viral vectors that can be produced by antibody libraries include RNA viruses and DNA viruses such as adenoviruses, adeno-associated viruses, herpes viruses, vaccinia viruses, pox viruses, sindbis viruses, sendai viruses, SV40 and HIV.

The antibody libraries can be constructed by known methods (see for example, McCafferty et al., Nature 348: 55-554 (1990); Clackson et al., Nature 352: 624-628 (1991); Marks et al., J. Mol. Biol. 222: 582-597 (1991), etc). More specifically, antibody libraries can be constructed as follows, but the construction methods are not limited to these. First, mice are immunized with either A-chain or B-chain receptors, and mRNAs are extracted from the splenocytes of these animals. The L-chain and H-chain variable regions are then recovered by RT-PCR using primers that correspond to mice CDRs. Single chain variable regions (scFv) are synthesized using assembly PCR to construct antibody libraries. Antigen-binding antibody clones are concentrated by panning, these single chain variable regions obtained from concentrated clones are inserted between a signal sequence for animal cells and CH1-hinge-CH2-CH3, and plasmids into which libraries are incorporated for generating retroviruses are constructed. Alternatively, scFab is synthesized, and libraries inserted between a signal sequence and hinge-CH2-CH3 are constructed. scDb libraries can also be made.

The antibody libraries of the present invention can also be constructed using plasmid expression vectors. Examples of expression vectors when the above cells are animal cells include pME18S (Med. Immunol. 20: 27-32 (1990)), pEF-BOS (Nucleic Acids Res. 18: 5322 (1990)), pCDM8 (Nature 329: 840-842 (1987)), pRSVneo, pSV2-neo, pcDNAI/Amp (Invitrogen), pcDNAI, pAMoERC3Sc, pCDM8 (Nature 329: 840 (1987)), pAGE107 (Cytotechnology 3: 133 (1990)), pREP4 (Invitrogen), pAGE103 (J. Biochem. 101: 1307 (1987)), pAMoA, pAS3-3, pCAGGS (Gene 108: 193-200 (1991)), pBK-CMV, pcDNA3.1 (Invitrogen), and pZeoSV (Stratagene). Expression promoters may be cytomegalovirus IE gene promoter and enhancer, SV40 early promoter, a retrovirus LTR such as that from RSV, HIV, and MMLV, and a gene promoter from animal cells such as metallothionein, β-actin, elongation factor-1, HSP genes, and such. Alternatively, viral vectors may be used as above. Viral vectors may be DNA viruses and RNA viruses such as retroviruses, adenoviruses, adeno-associated viruses, herpes viruses, vaccinia viruses, poxviruses, Simbu viruses, Sendai viruses, SV40, and HIV.

The methods for introducing plasmid expression vectors may vary depending on the type of cell and vector. Any method can be used as long as expression vector DNA can be introduced into cells. For example, the methods include electroporation (Cytotechnology 3: 133 (1990)), calcium phosphate (JP-A Hei 2-227075), lipofection (Proc. Natl. Acad. Sci. USA 84: 7413 (1987); Virology 52: 456 (1973)), co-precipitation with calcium phosphate, DEAE-dextran, direct injection of DNA using microcapillaries, and such.

Furthermore, where the receptors are heteroreceptors (where the antibodies are multi-specific antibodies), expression of the test antibodies of the present invention is usually possible by introducing, into one cell, expression libraries (vectors) for each of the two types of light chains and two types of heavy chains. No compatibility is usually present for the light and heavy chain combinations. For four chains, there are ten types of combinations. The agonistic antibodies finally screened by the methods of the present invention are preferably whole antibodies that are stable in the blood. Thus, it is preferable that the test antibodies used in the screening methods of the present invention are also full length. When, as above, libraries are expressed in cells as is, ten different types of antibodies are secreted. Due to the potential of neutralizing effects by other antibody combinations, it is preferable to express test antibodies that comprise the desired combination of heavy and light chains. To get the desired combination, for example, a common light chain is preferably used. Alternatively, to avoid homogenous combinations of heavy chains, it is also possible to encourage heterogeneous combination using amino acid substitution to introduce "knobs-into-holes" (Protein Engineering Vol. 9, 617-621, 1996; WO98/50431) at heavy chain CH3 regions, thus blocking the formation of heavy chain homodimers. Thus in the present invention, test antibody CH3s are preferably characterized by the introduction of "knobs-into-holes" by amino acid substitution. Appropriate amino acid substitutions are carried out in the CL and CH1, and by defining the combinations of light and heavy chains, the production efficiency of hetero-antibodies can be raised. Furthermore, combinations of light and heavy chains can be defined using scFv single-chain variable regions that link the light and heavy chain variable regions with linkers. Test antibodies can also be expressed in the form of scFv-CH1-hinge-CH2-CH3. Therefore, in one embodiment of the present invention, the test antibodies are characterized by the linking of their light and heavy chain variable regions by linkers. These multi-specific test antibodies with variable regions linked by linkers can be produced, for example, as below. However, production is not particularly limited to these methods.

(1) A single chain Fv against the first receptor chain is produced. Next, by linking that single chain Fv with CH1-hinge-CH2-CH3, a single chain antibody against the first receptor chain is produced. Test antibodies comprising that single chain antibody are then produced.

(2) A single chain Fab against the first receptor chain is produced. Next, by linking that single chain Fab with Fc, a single chain antibody against the first receptor chain is produced. Test antibodies comprising that single chain antibody are then produced.

In addition, the present invention's screening methods for multi-specific agonistic antibodies can be provided by using multi-specific antibodies, produced by known manufacturing methods, as test antibodies.

The "contact" of test antibodies and receptors in the above step (a) in the present invention can refer to, for example, the "contact" of receptors expressed in the cells with test antibodies expressed in and secreted out of the cells as mentioned above. However, "contact" is not particularly limited to this form of contact.

In the above-mentioned screening methods of the present invention, whether or not a test antibody comprises agonistic activity is then determined (step b), and antibodies comprising agonistic activity are selected (step c).

In the above-mentioned steps in a preferable embodiment of the present invention, whether or not test antibodies comprise agonistic activity is judged by using the presence or absence of the above-mentioned autonomous autocrine cell replication as an index. Where there is autonomous autocrine cell replication, antibodies expressed by those cells are selected as agonistic antibodies.

Agonistic antibodies selected in the screening methods of the present invention are usually recovered from cells with autonomous autocrine replication, and cloned accordingly. These cells are used to recover the CDR genes of the above-mentioned multi-specific agonistic antibodies by PCR, and these recovered genes can then be used for antibody production. One skilled in the art can use routine procedures to ordinarily carry out the production of antibodies based on the CDR genes.

Where the receptor is a heteroreceptor, the screening methods for multi-specific antibodies of the present invention can be carried out specifically as below. However, this method is one embodiment of the present invention, and the methods of the present invention are not especially limited to this method.

Antibody phage libraries are produced from animals immunized with the extracellular region of receptor chains that use antibodies as ligands (e.g. the A chain and B chain). Anti-receptor chain antibodies are selected by panning, and then transformed to retroviral vector libraries.

Next, a cell line that proliferates ligand-dependently is prepared. An anti-A-chain antibody library is introduced into these cells by infection, and infected cells are selected using a drug-resistant gene incorporated into the vector. Selected cells are then cultured and subsequently, super-infected with the anti-B-chain antibody library. In this way, a library of cells expressing bispecific antibodies of every anti-A-chain antibody and anti-B-chain antibody combination can be constructed. Of these, only clones that secrete appropriately combined bispecific antibodies showing agonistic activity against a target receptor can autonomously replicate upon autocrine stimulation. In this way, the engineered antibody genes can be recovered by PCR from the chromosomes of selected BaF3 clones.

Methods of screening for antibodies that comprise agonistic activity by using autonomous autocrine growth were unknown until now, and hence were newly discovered by the present inventors. The present invention provides agonistic antibody screening methods that use autonomous autocrine replication due to common antibodies, including multi-specific antibodies.

The above-mentioned screening methods first provide cells that express a test antibody and a receptor that multimerizes, where the growth of those cells depends on a ligand (factor) of that receptor (step A). Next, where the cells undergo autonomous autocrine replication, the test antibodies are judged to comprise agonistic activity (step B). Antibodies that comprise agonistic activity are then selected (step C).

The above-mentioned methods are not particularly limited to the screening of multi-specific agonistic antibodies, and screening for agonistic antibodies that do not show multi-specificity is also comprised in the above-mentioned methods.

It is commonly known that light chains do not have much effect on antibody specificity. Thus, even when antibodies are multi-specific, the above-mentioned methods can be carried out without introducing two types of heavy chains and two types of light chains into cells. The above-mentioned methods can also be carried out by introducing two kinds of heavy chain libraries into cells after pre-expressing one kind of light chain. Thus, a preferable embodiment of the present invention, in addition to steps (A) to (C), comprises the step of introducing genes that code for a test antibody's heavy chain into the cells of step (A), which have been introduced with a gene coding for the receptor, and a gene coding for the test antibody's light chain.

In addition, the present invention provides methods for producing agonistic antibodies that use the methods of screening for agonistic antibodies of the present invention.

In the above methods, agonistic antibodies are first screened by the methods of screening for agonistic antibodies of the present invention, and genes that code for the agonistic antibodies selected by this screening are introduced into host cells. Multi-specific agonistic antibodies are then recovered from those host cells or their culture supernatant.

The antibodies of the present invention, obtained as above, can be isolated using signal sequences from inside cells, or from the culture medium if secreted into the extracellular space. They can then be purified as substantially pure polypeptides. Separation and purification of polypeptides can be performed by appropriately selecting or combining methods as necessary. Separation methods can be selected from those generally used, such as chromatography, filtration, ultrafiltration, salting out, solvent precipitation, solvent extraction, distillation, immunoprecipitation, SDS-polyacrylamide gel electrophoresis, isoelectric point focusing, dialysis, and recrystallization. Chromatography includes affinity chromatography, ion exchange chromatography, hydrophobic chromatography, gel filtration, reverse phase chromatography, absorption chromatography, and the like (Strategies for Protein Purification and Characterization: A Laboratory Course Manual, Daniel R. Marshak et al. eds., Cold Spring Harbor Laboratory Press (1996); Antibodies: A Laboratory Course Manual, Harlow and David Lane eds., Cold Spring Harbor Laboratory Press (1988)). Such chromatographies may be performed using liquid chromatographies such as HPLC, FPLC, and the like. In addition, since the antibodies of the present invention bind antigens, they may be purified by making use of this ability. Agonistic antibodies isolated and purified in this way are themselves included in the present invention.

The test antibodies in a preferable embodiment of the present invention have their heavy and light chain variable regions linked by linkers, and are introduced with "knobs-into-holes" by amino acid substitution at CH3. Thus, the antibodies provided by the present invention are preferably agonistic antibodies that are characterized by having their heavy and light chain antibody variable regions linked by linkers, and that are introduced with "knobs-into-holes" by amino acid substitution at CH3 of the antibodies.

In the screening methods of the present invention, the agonist activity that can be used as a detection index is preferably proliferation activity. However, it is also possible to use, for example, changes in the amount and/or type of substance produced (secretary proteins, surface antigens, intracellular proteins, mRNA, etc.), anchorage dependency, cytokine-dependant responsiveness, hormone dependency, drug resistance, cell motility, cell migration activity, pulsatility, changes in intracellular substance, protein phosphorylation, etc.

Agonistic antibodies that can be acquired by the screening methods of the present invention can be used as pharmaceutical agents for immunotherapy or prevention, in the same way as traditionally known multi-specific antibodies. IL-10, 12, 24, 4, 7, 9, 13, TSLP, IFNα, β and such are known as ligands for immune system receptors made up of heterodimers. NGF, GDNF, NT-3, 4 and 5 are known as ligands for nervous system receptors. Antibodies acquired by the methods of the present invention can be, for example, antibodies that comprise an above-mentioned ligand-like function. The antibodies acquired by the methods of the present invention are expected to become pharmaceuticals for therapy of immune or nervous system illnesses and such.

Pharmaceutical compositions used for such therapeutic or preventive purposes, which comprise antibodies of the present invention as active ingredients, may be formulated by mixing with suitable pharmaceutically acceptable carriers and solvents, if necessary, that are inactive against the antibodies. For example, sterilized water, saline, stabilizers, vehicles, antioxidants (e.g. ascorbic acid), buffers (e.g. phosphate, citrate, other organic acids), preservatives, detergents (e.g. PEG, Tween), chelating agents (e.g. EDTA), and binders may be used. Alternatively, they may comprise other low molecular weight polypeptides, proteins such as serum albumin, gelatin and immunoglobulins, amino acids such as glycine, glutamine, asparagine, arginine, and lysine, carbohydrates and sugars such as polysaccharides and monosaccharides, and sugar alcohol such as mannitol and sorbitol. When prepared as an aqueous solution for injection, saline and isotonic solutions comprising glucose and other adjunctive agents such as D-sorbitol, D-mannose, D-mannitol, and sodium chloride may be used. In addition, an appropriate solubilizing agent such as alcohol (e.g. ethanol), polyalcohol (e.g. propylene glycol, PEG), and non-ionic detergents (e.g. polysorbate 80, HCO-50) may be used in combination.

If necessary, antibodies of the present invention may be encapsulated in microcapsules (microcapsules made of hydroxycellulose, gelatin, polymethylmethacrylate, and the like), and made into components of colloidal drug delivery systems (liposome, albumin microsphere, microemulsion, nano-particles, and nano-capsules) (refer to, for example, "Remington's Pharmaceutical Science 16th edition", Oslo Ed. (1980)). Moreover, methods for making sustained-transduce drugs are known, and these can be applied for the antibodies of the present invention (Langer et al., J. Biomed. Mater. Res. 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP: 133,988).

Administration to patients may be preferably performed by injections or intravenous drips; for example, in addition to intra-arterial injections, intravenous injections, and subcutaneous injections, methods known to one skilled in the art may be used, such as administrating intranasally, intrabronchially, intramuscularly, percutaneously, or orally. Doses may vary depending on various factors, including patient body weight and age, type of disease, symptoms, and administration method, but those skilled in the art are able to appropriately select suitable doses.

In addition, genes encoding antibodies of the present invention may be used for gene therapy by cloning into vectors for such use. Such vectors can be administered by direct injection using naked plasmids, and also by packaging in liposomes, producing as a variety of viral vectors such as retrovirus vectors, adenovirus vectors, vaccinia virus vectors, poxvirus vectors, adenoassociated virus vectors, and HVJ vector (Adolph, "Virus Genome Methods", CRC Press, Florida (1996)), or coating onto carrier beads such as colloidal gold particles (e.g. WO93/17706). However, any method can be used for administration as long as the antibodies are expressed in vivo and exercise their function. Preferably, a sufficient dose may be administered by a suitable parenteral route (such as injecting intravenously, intraventricularly, subcutaneously, percutaneously, or into adipose tissues or mammary glands, inhalation, intramuscular injection, infusion, gas-induced particle bombardment (using electron gun and such), or through the mucosa (for example, by nose drops). Alternatively, genes encoding antibodies of the present invention may be administered into, for example, blood cells and bone marrow cells ex vivo using liposome transfection, particle bombardment (U.S. Pat. No. 4,945,050), or viral infection, and the cells may be reintroduced into animals.

BEST MODE FOR CARRYING OUT THE INVENTION

Figure 1:
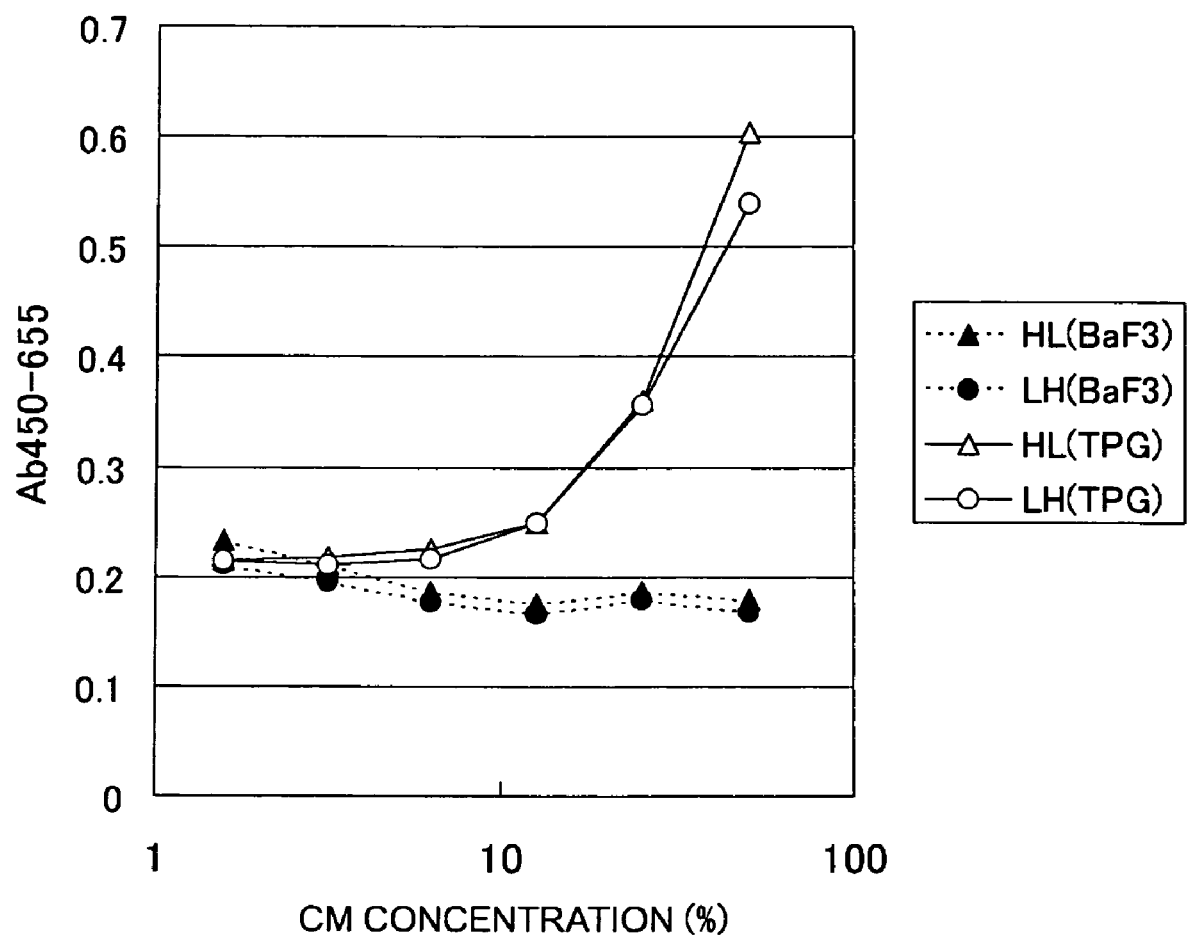
FIG. 1 is a graph showing Conditioned medium (CM)-dependent growth of an autonomously replicating cell line. 200 μL of various concentrations of culture supernatants of MPL-expressing BaF3 cells that acquired autonomous replication by viral infection, was added to each well containing 10,000 washed MPL-expressing BaF3 cells (cells expressing chimeric receptors of the MPL extracellular region, and GCSF receptor transmembrane/intracellular region: TPG). After three days, 20 μL of SF reagent (Nacarai Tesque) for measuring the viable cell number was added. After two and a half hours, absorbance was measured at 450 nm, and the number of viable cells was investigated. MPL-expressing BaF3 cells (HL(TPG) and LH(TPG)) maintained cell growth in a culture supernatant concentration-dependant manner. On the other hand, parent cell lines BaF3 (HL(BaF3) and LH(BaF3)), which do not express receptors, did not grow, since the antibodies do not act on these cells. The x-axis shows Conditioned medium (CM) concentration (%). The z-axis shows absorbance at 450-655 nm.

Herein below, the present invention will be specifically described with reference to Examples, but it is not to be construed as being limited thereto.

EXAMPLE 1

Autocrine Growth by Diabodies

As a model of agonistic antibodies, the anti-mpl-monoclonal antibody 12E10 (WO99/10494) was used. An EcoRI-NotI fragment encoding a diabody was excised from pCOSsc12E10 (WO01/79494, WO02/33072) encoding the antibody 12E10 variable region. This fragment was inserted between the EcoRI and NotI of viral vector plasmid pMX. This plasmid pMXsc12E10 was transfected into Pt—B packaging cells using FuGene6 (Roche). Pt—B cells were seeded in 6 cm dishes containing Dulbecco's Modified Eagle Medium (DMEM) with 10% fetal calf serum (FCS). The next day a mixture of FuGene6 and plasmid pMXsc12E10 was added to the culture. A day after that, the culture medium was replaced, and the culture supernatant was collected after 24 hours. 10 μg/mL of Polybrene (Hexadimethrine Bromide, Sigma) was added to culture supernatant containing the recombinant virus, target cells were suspended in this culture supernatant and infected. Human MPL cDNA was introduced into ligand (factor)-dependent cell line BaF3. Cell line MPL/BaF3 (cells expressing chimeric receptors of the MPL extracellular region, and GCSF receptor transmembrane/intracellular region), which can grow due to the addition of MPL ligand (thrombopoietin), was infected by adding a viral solution with mouse interleukin-3 (IL-3). The next day the cells were washed with PBS. Culture was continued in IL-3-free RPMI with 10% FCS, and autonomously replicating cells were obtained. Where the culture supernatant of these cells was collected and added to different MPL/BaF3 for incubation, a cell growth dependant on the concentration of the added culture supernatant was observed. From this it was clear that the autonomous replication of virus-infected cells was due to the autocrine stimulation of diabodies secreted into the culture medium by these cells.

EXAMPLE 2

Autocrine Growth by scFv-CH1-Fc

PCR was carried out using pCOSsc12B5 as a template, and primers EcoRI-HL (5'-GGAATTCGCCGCCACCATG-GAGTTTGGGCTGAGCTGGGTTTTCCT-3': SEQ ID NO: 1) and HL-SfiI (5'-GCATGCATGGCCCCCGAGGCCACT-CACCTTTGATCTCCAGCTTGGTCCCTCCGCCGAA-3': SEQ ID NO: 2). An scFv (H-L) gene comprising an EcoRI site at its 5' and a splice donor sequence and SfiI site at its 3' was obtained. In addition, to obtain a gene connected in the light-heavy (L-H) chain order, PCR was carried out using pCOSsc12B5 as a template, and a primer combination of 5Hs(5'-GGCGGCGGCGGCTCCGGTGGTGGTG-GATCCCAGGTGCAGCTGGTGCAGTCTGG-3': SEQ ID NO: 3) and 3Ha-SfiI (5'-GCATGCATGGCCCCCGAGGC-CACTCACCTGAAGAGACGGTGACCATTGTCCCTT-3': SEQ ID NO: 4); or 5Ls(5'-AGTCAGTCGGCCCAGCCG-GCCATGGCGGACTACAAAGACATCCA-GATGACCCAGTCTCCT-3': SEQ ID NO: 5) and 3La (5'-GGAGCCGCCGCCGCCAGAACCACCACCACCAGAA-CCACCACCACCTTTGATCTCCAGCTTGGTC CCTC-CGCCGAAA-3': SEQ ID NO: 6). By again carrying out PCR on both obtained amplification products using primers 5Hs and 3La, the amplification products were assembled. The produced LH comprised an SfiI site on both ends, and a splice donor site at the 3' side.

PCR was carried out using plasmid HEF-1.24H-gγ1 (WO99/18212) as a template, which comprises a human IgG1 constant region gene. The intron before CH1 and CH1; hinge (primers EcoSfiI (5'-TCGAATTCGGCCTCGGGGGC-CAGCTTTCTGGGGCAGGCCAGGCCTGAC-CTTGGCTTT-3': SEQ ID NO: 7), and HigeCH1a (5'-CACG-GTGGGCATGTGTGAGTTTTGTCACAAGATTTGGGC-TCAACTTTCTTGTCCACCTTG-3': SEQ ID NO: 8)); CH2 (primers HigeCh2s (5'-CAAAACTCACACATGCCCAC-CGTGCCCAGCACCTGAACTCCTGGGGG-GACCGTCAGTCTT-3': SEQ ID NO: 9), and Ch3Ch2a (5'-ACACCTGTGGTTCTCGGGGCTGCCCTTTGGCTTTG-GAGATGGTTTTCTCGATG-3': SEQ ID NO: 10)); CH3 (primers Ch2Ch3sW (5'-GGCAGCCCCGAGAACCACAG-GTGTACACCC-3': SEQ ID NO: 11), and StopNotI (5'-TAGCGGCCGCTCATTTACCCGGAGA-CAGGGAGAGGCTCTT-3': SEQ ID NO: 12)) were amplified. By continuing with this assembly PCR, an IgG1 constant region gene comprising an EcoRI site, an SfiI site, and an intron at its 5', and a NotI site at its 3' was constructed.

PCR was carried out using mouse interleukin (IL)-3 cDNA as a template, and primers IL3sEcoA (5'-CGGAATTCGGC-CGGCTGGGCCAGCATCAGGAGCAGGAGCAGC-3': SEQ ID NO: 13), and BamIL3ss (5'-GCGGATCCGCCGC-CACCATGGTTCTTGCCAGCTCTAC-3': SEQ ID NO: 14), and an IL3 signal sequence (ss) gene comprising a BamHI site at its 5', and an SfiI site and EcoRI site at the 3' was obtained.

The synthesized IgG1 constant region gene was inserted in the EcoRI-NotI site of a retroviral vector pMX, and pMX-CHwild was constructed. pMX-HL-CHwild was obtained by incorporating the scFv (H-L) gene into the EcoRI-SfiI site of the pMX-CHwild plasmid. When the virus derived from this plasmid infects cells, molecules used as antibodies, which have CH1-hinge-CH2-CH3 linked with the scFV (H-L) C-terminal of antibody 12B5, can be expected to be secreted. Then, IL3ss was incorporated into the BamH1-EcoRI site of pMX-CHwild, and scFv (L-H) was further incorporated into the SfiI site to construct pMX-IL3ss-LH-CHwild. ScFv-CH1-hinge-CH2-CH3 (L-H) can be expected to be secreted by this plasmid-derived virus. The above plasmids were respectively transfected into Pt-E cells, as above. Recombinant viruses were obtained and used to infect MPL/BaF3 cells. The next day, IL-3 was removed by washing, and culture was continued. As a result, cells that can replicate autonomously were obtained. The culture supernatant of these cells was collected, and on culturing with different MPL/BaF3s, cell growth dependant on the concentration of culture supernatant added was observed (FIG. 1, TPG). On the other hand, parent line BaF3 did not express the receptors, and thus did not proliferate as antibodies did not act on them (FIG. 1, BaF3). From this, the autonomous replication of virus-infected cells was revealed to be due to the autocrine stimulation of scFv-CH1-hinge-CH2-CH3 secreted into the medium by those cells.

INDUSTRIAL APPLICABILITY

The present invention provides novel methods that can effectively screen for agonistic antibodies. In a preferable embodiment of the present invention, screening is made easily possible by using antibodies as libraries, without the need for complicated procedures. In addition, in a preferable embodiment of the present invention, autonomous autocrine replication is used as an index for screening. Since only clones that secrete agonistic antibodies themselves are selected as cells that have reproduced via receptor signals, multiple samples (antibody libraries) can be treated simultaneously, and extremely effectively.

The invention claimed is:

1. A method of screening for agonistic antibodies, the method comprising:
   (a) providing a cell that expresses both a multimer-forming receptor and a test antibody, wherein the cell in the absence of the antibody requires a ligand of the receptor for growth;
   (b) culturing the cell in the absence of the ligand; and
   (c) selecting the test antibody as an agonist of the receptor if the cell grows in the absence of the ligand.

2. The method of claim 1, flirt her comprising the steps of (i) providing a cell comprising a nucleic acid encoding the light chain of the antibody and a nucleic acid encoding the receptor; and (ii) introducing into the cell a nucleic acid that encodes the heavy chain of the test antibody, thereby producing the cell of step (a).

3. The method of claim 1, wherein the receptor is a chimeric receptor that functions to transduce a cell growth signal.

4. The method of claim 1, wherein the receptor is a dimer-forming receptor.

5. The method of claim 4, wherein the dimer-forming receptor is a homo-dimer-forming receptor.

6. The method of claim 4, wherein the dimer-forming receptor is a hetero-dimer-forming receptor.

7. The method of claim 1, wherein the receptor is a G-CSF receptor.

8. The method of claim 1, further comprising a step of producing a plurality of cells expressing a library of diverse antibodies, the cell of step (a) being a member of the plurality of cells.

9. The method of claim 8, wherein the library of diverse antibodies is encoded by a retroviral antibody library introduced into the plurality of cells.

10. The method of claim 1, wherein the test antibody is a multi-specific antibody.

11. The method of claim 10, wherein the test antibody comprises heavy and light chain variable regions connected via a linker.

12. The method of claim 11, further comprising expressing the test antibody by a method that comprises:

(i) producing a first DNA encoding a single chain Fv that binds to the receptor;
(ii) producing a second DNA encoding a single chain antibody comprising the single chain Fv of step (i) linked to a CH1-hinge-CH2-CH3; and
(iii) expressing a multi-specific antibody that comprises the single chain antibody of step (ii).

13. The method of claim 11, further comprising expressing the test antibody by a method that comprises:
(i) producing a first DNA encoding a single chain Fab that binds to the receptor;
(ii) producing a second DNA encoding a single chain antibody comprising the single chain Fab of step (i) linked to an Fc; and
(iii) expressing a multi-specific antibody that comprises the single chain antibody of step (ii).

14. A method of screening for agonistic antibodies, the method comprising:
providing an antibody expression library of cells, the cells each expressing both a member of a set of diverse antibodies and a multimer-forming receptor, wherein the cells in the absence of the antibodies require a ligand of the receptor for cell growth;
culturing the library of cells in the absence of the ligand;
selecting a cell that grows in the absence of the ligand; and
identifying the antibody expressed by the selected cell as being an agonist of the receptor.

15. The method of claim 14, wherein the antibody expression library comprises a retroviral antibody library.

* * * * *

UNITED STATES PATENT AND TRADEMARK OFFICE
CERTIFICATE OF CORRECTION

PATENT NO. : 7,732,149 B2 Page 1 of 1
APPLICATION NO. : 10/511993
DATED : June 8, 2010
INVENTOR(S) : Tetsuo Kojima et al.

It is certified that error appears in the above-identified patent and that said Letters Patent is hereby corrected as shown below:

Title Page, Item (54): "METHODS OF SCREENING AGONISTIC ANTIBODIES"
should read --METHODS OF SCREENING FOR AGONISTIC ANTIBODIES--.

Column 21, line 57, claim 1, "flirt her comprising" should read --further comprising--.

Signed and Sealed this

Twenty-eighth Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,732,149 B2 | Page 1 of 1 |
| APPLICATION NO. | : 10/511993 | |
| DATED | : June 8, 2010 | |
| INVENTOR(S) | : Tetsuo Kojima et al. | |

It is certified that error appears in the above-identified patent and that said Letters Patent is hereby corrected as shown below:

Title Page, Item (54) and at Column 1, lines 1 and 2, title: "METHODS OF SCREENING AGONISTIC ANTIBODIES" should read --METHODS OF SCREENING FOR AGONISTIC ANTIBODIES--.

Column 21, line 57, claim 1, "flirt her comprising" should read --further comprising--.

This certificate supersedes the Certificate of Correction issued September 28, 2010.

Signed and Sealed this

Ninth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,732,149 B2 | Page 1 of 1 |
| APPLICATION NO. | : 10/511993 | |
| DATED | : June 8, 2010 | |
| INVENTOR(S) | : Kojima et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 921 days.

Signed and Sealed this

Seventh Day of December, 2010

David J. Kappos
*Director of the United States Patent and Trademark Office*